(12) United States Patent
Labrecque et al.

(10) Patent No.: US 11,285,232 B2
(45) Date of Patent: Mar. 29, 2022

(54) WASTE BIN ODOR CONTROL METHOD AND SYSTEM

(71) Applicant: IPL INC., St-Damien-de-Buckland (CA)

(72) Inventors: Jean-Gabriel Labrecque, St-Damien-de-Buckland (CA); Yvan Marcoux, St-Joseph-de-Beauce (CA)

(73) Assignee: IPL INC.

( * ) Notice: Subject to any disclaimer, the term of this patent is extended or adjusted under 35 U.S.C. 154(b) by 0 days.

(21) Appl. No.: 16/609,991

(22) PCT Filed: Mar. 14, 2019

(86) PCT No.: PCT/CA2019/050315
§ 371 (c)(1),
(2) Date: Oct. 31, 2019

(87) PCT Pub. No.: WO2019/173922
PCT Pub. Date: Sep. 19, 2019

(65) Prior Publication Data
US 2021/0275712 A1 Sep. 9, 2021

Related U.S. Application Data

(60) Provisional application No. 62/642,747, filed on Mar. 14, 2018.

(51) Int. Cl.
*A61L 9/01* (2006.01)
*B65F 1/14* (2006.01)

(52) U.S. Cl.
CPC .................... *A61L 9/01* (2013.01); *B65F 1/14* (2013.01); *A61L 2209/15* (2013.01); *B65F 2210/129* (2013.01)

(58) Field of Classification Search
None
See application file for complete search history.

(56) References Cited

U.S. PATENT DOCUMENTS

| 4,802,626 A | 2/1989 | Forbes et al. | |
| 2011/0209276 A1* | 9/2011 | Lu | C11D 17/0056 4/223 |

OTHER PUBLICATIONS

The Soap Brewhouse-Making of Blueberry Soap Shooters (soap on a rope), Youtube.com [online video] [retrieved on Jul. 20, 2021]. https://www.youtube.com/watch?v=en2qwjTU-qw (Year: 2017).*
Buzzfeed Nifty-DYI Loofah Soap Bars, Youtube.com [online video] [retrieved on Jul. 21, 2021]. https://www.youtube.com/watch?v=pF6UEOqXOug (Year: 2018).*

(Continued)

*Primary Examiner* — Jelitza M Perez
(74) *Attorney, Agent, or Firm* — Lavery, De Billy, LLP; Gwendoline Bruneau

(57) ABSTRACT

A method for making a waste bin odor-controlling pad configured to be hung within the waste bin by a connector, comprising providing a mold; providing a connector; positioning a first length of the connector within a mold at a predetermined position within the mold, while keeping a second length of the connector outside the mold; and pouring an active material within the mold; the predetermined position within the mold being selected based on the geometry of the pad to be made.

11 Claims, 18 Drawing Sheets

(56) References Cited

OTHER PUBLICATIONS

BuzzFeed Nifty-DYI Loofah Soap Bars, Youtube.com [online video] [retrieved on Oct. 28, 2021]. https://www.youtube.com/watch?v=pF6UEOqXOug (Year: 2018).*

Actalys—Traeatment and odor removal, http://www.actalys.eu/uk/traitement-des-odeurs.html, Jan. 23, 2018.

Air Wick Stick Ups Air Freshener—2-in-1, https://www.dealdey.com/deals/air-wick-stick-ups-air-freshener-2-in-1, Jan. 23, 2018.

Ecozone Toilet Smell Killer Register Interest, https://www.buymythings.com.au/productdisplay/ecozone-toilet-smell-killer, Jan. 23, 2018.

Febreze stick and refresh, https://www.amazon.ca/s/(ie=UTF8&keywords=febreze+stick+and+refresh&tag=googca, Jan. 23, 2018.

Garbage odor eliminator, https:///www.youtube.com/watch?v=IIX8ORywKrE.

Gonzo 4142 Garbage Odor Eliminator, https://www.amazon.ca/magic-natural-garbage-eleminator-ounce/dp/B0073VPH5M, Jan. 23, 2018.

Smoke Odor Eliminator, Febreze Car, https://www.febreze.com/en-us/products/car-air-fresheners-smoke-odor-eliminator, Jan. 23, 2018.

Tired of your home smelling like smoke? (OdoBan in Canada)—YouTube, https://www.youtube.com/embed/G_4IJ_9NCI?feature=oembed&wmode=opaque, Jan. 23, 2018.

Toter Launches New Line of Trash Cart Accessories for Consumers, http://www.prweb.com/releases/2017/02/prweb14025090.htm, Jan. 23, 2018.

X-o odor neutralizer, https://www.amazon.ca/s/?ie=UTF8&keywords=x-o+odor+neutralizer&tag=googcana-20, Jan. 23, 2018.

ZEP 16 oz. Garbage Odor Eliminator-ZUGOE1, The Home Depot, https://www.homedepot.com/p/ZEP-16-oz-Garbage-Oder-Eliminator-ZUGOE1/203487361, Jan. 23, 2018.

* cited by examiner

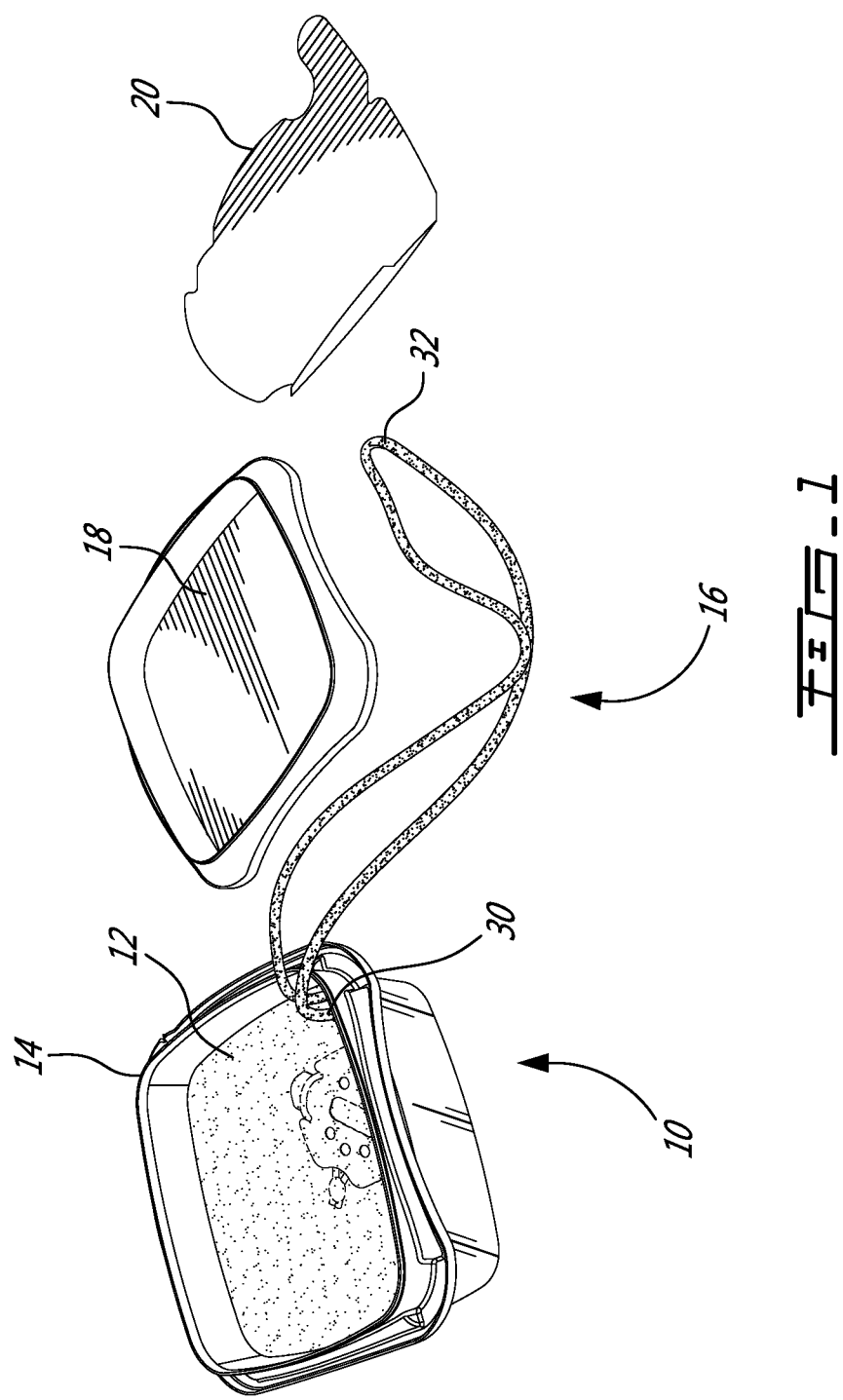

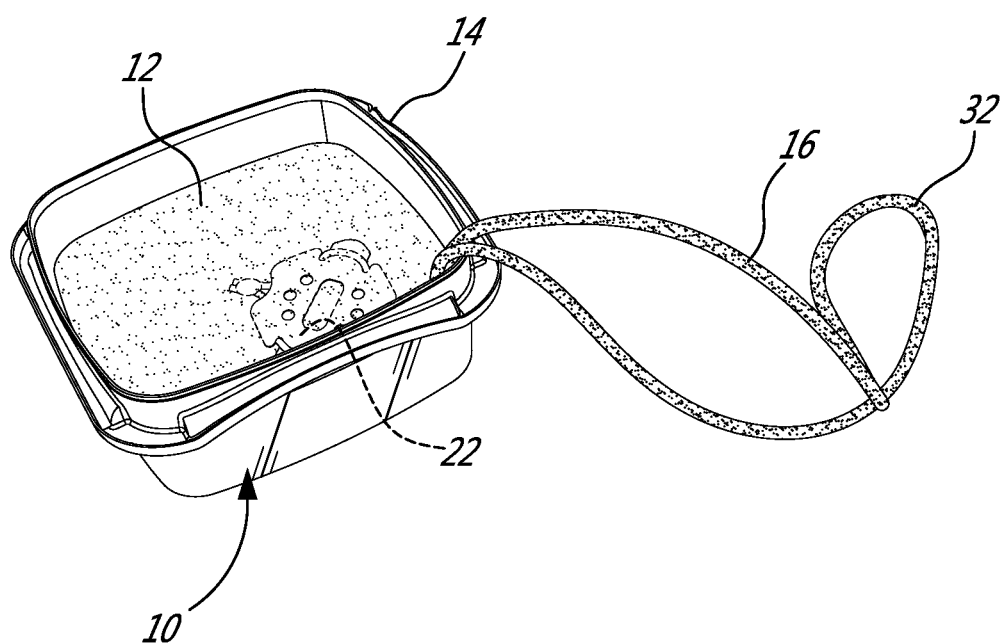
FIG_2

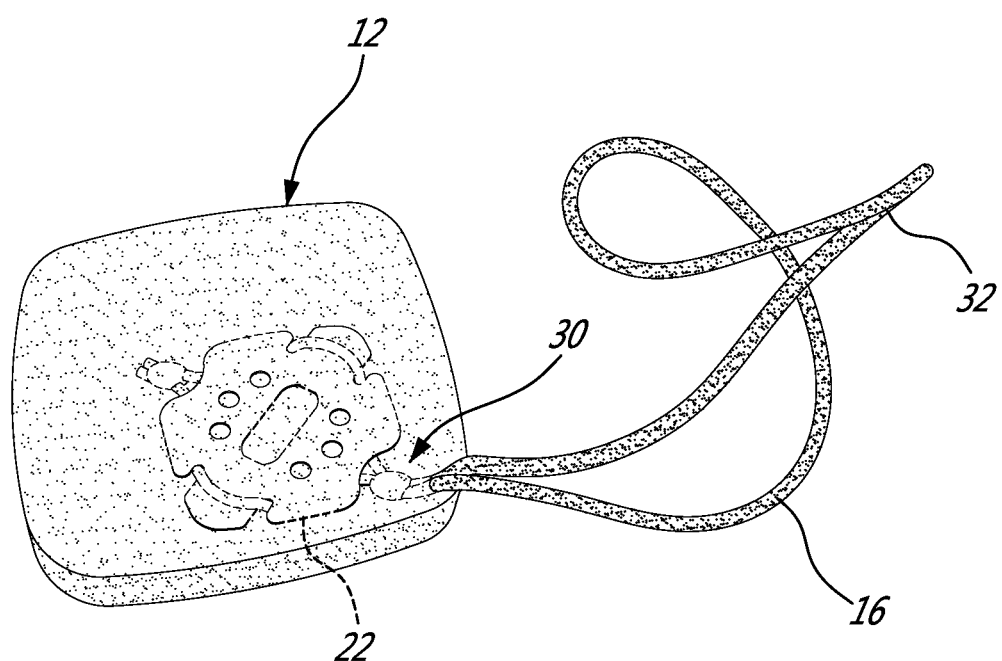
FIG_3

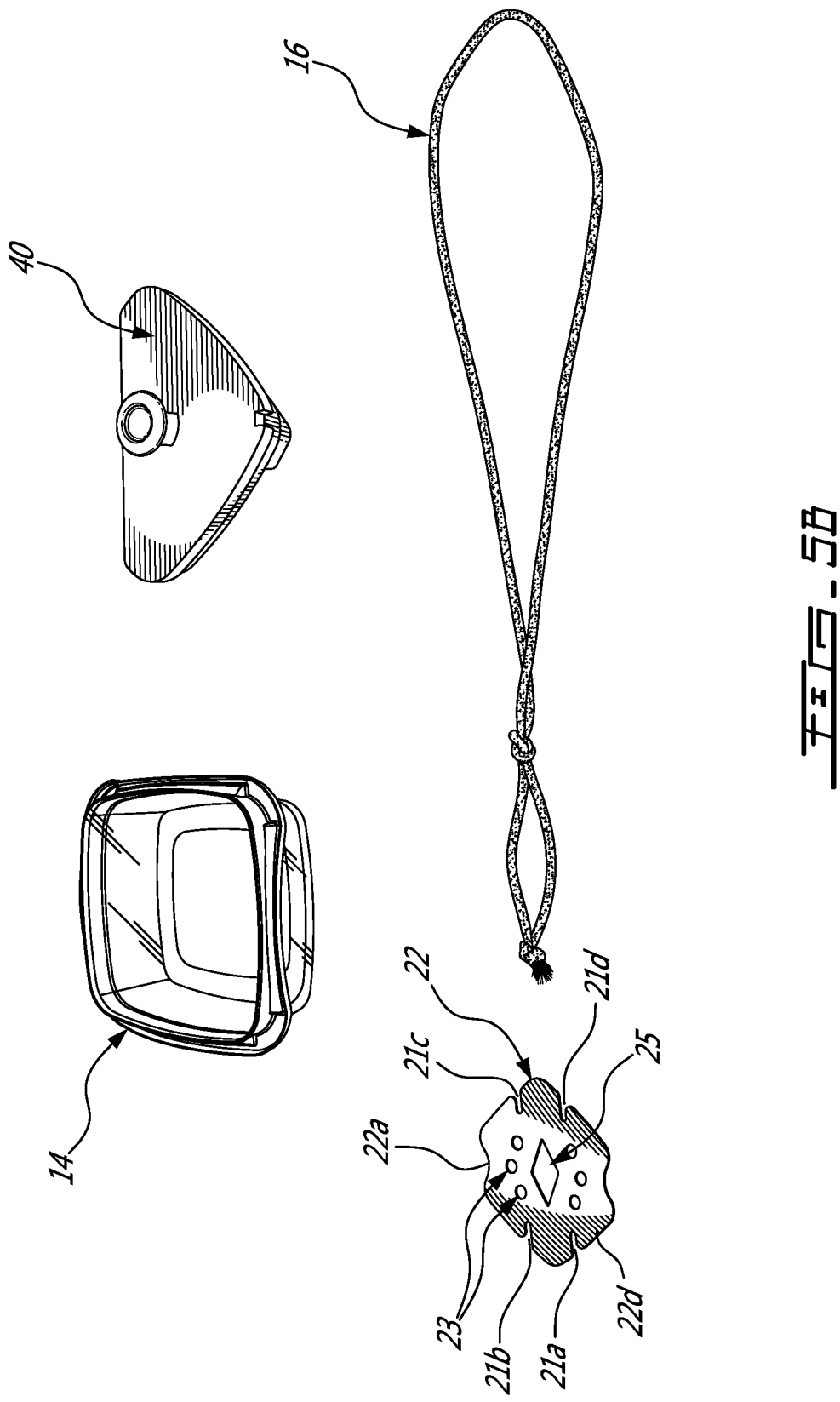

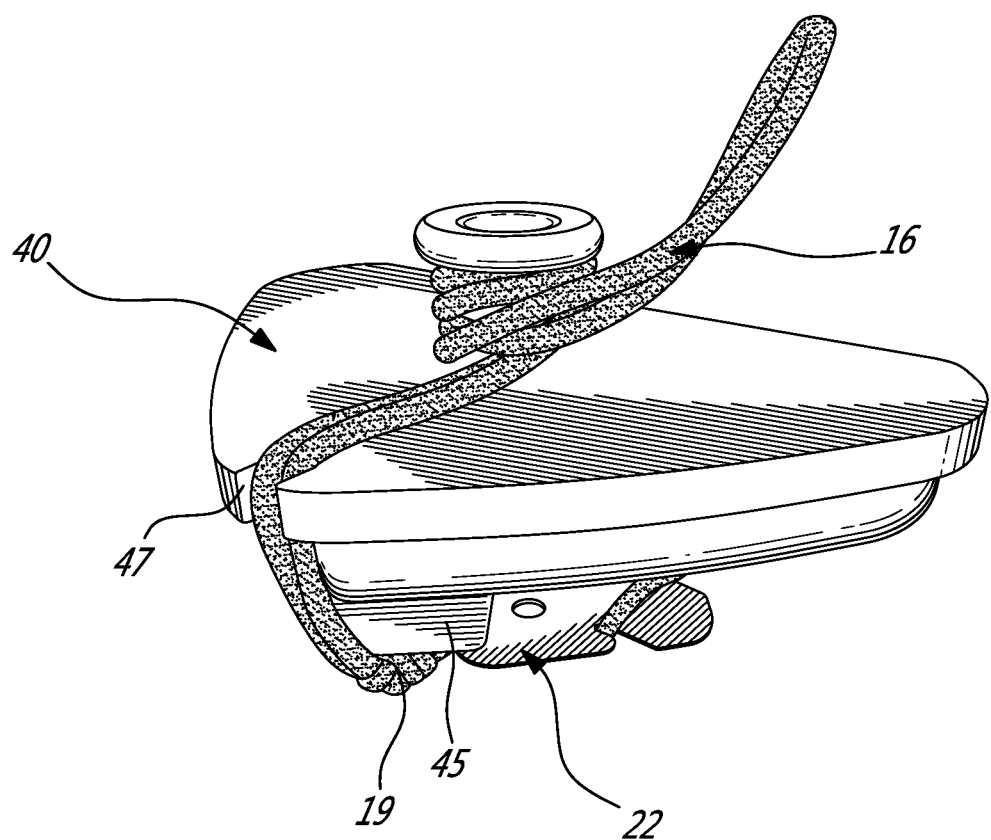
FIG_5E

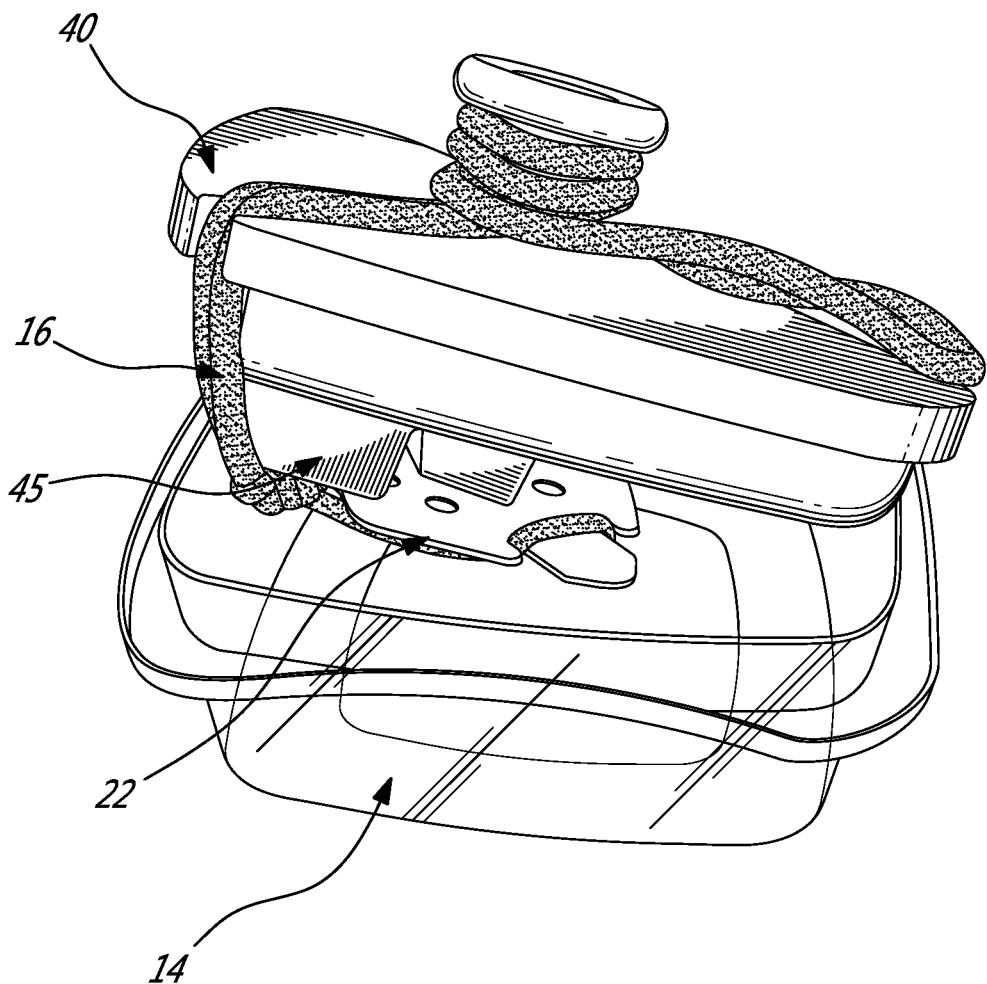
FIG_5F

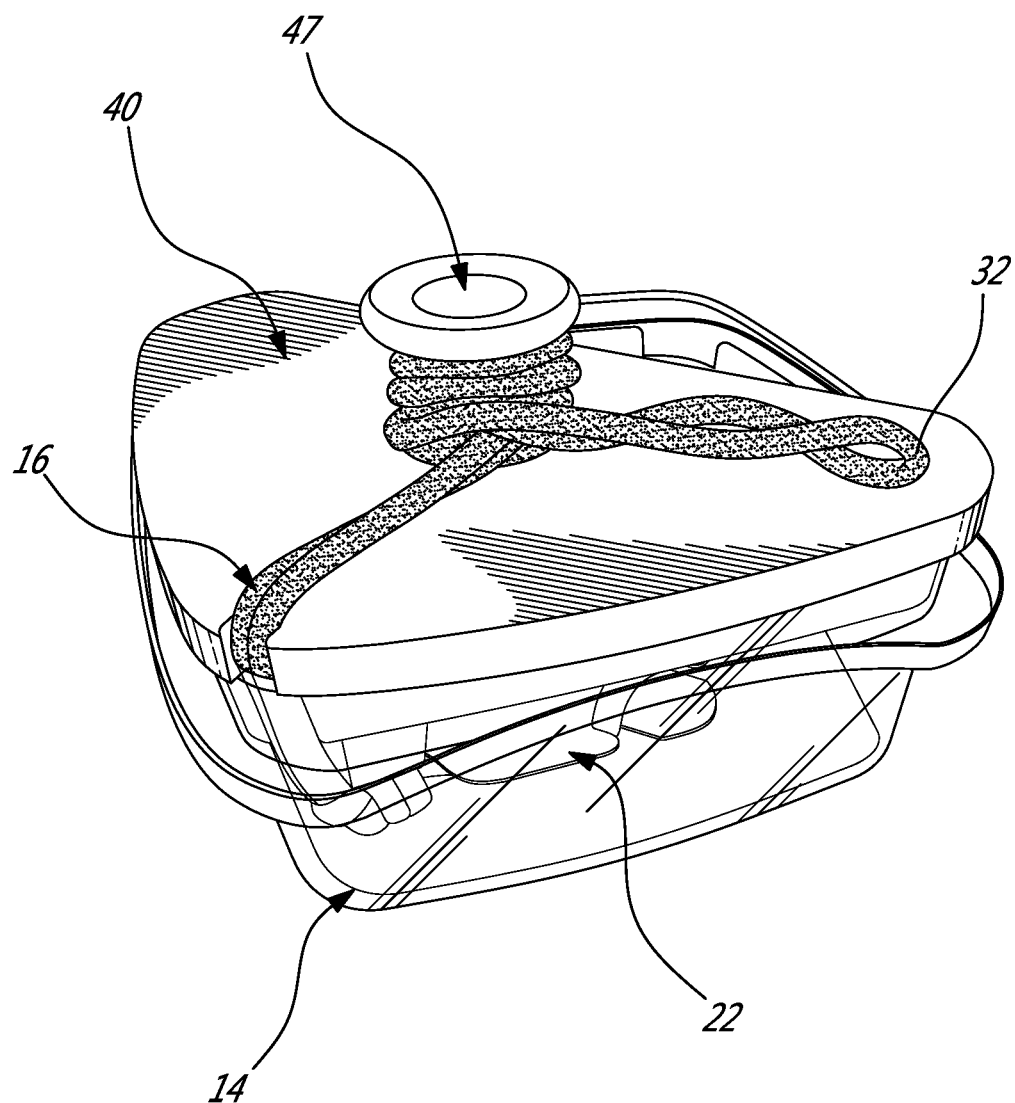
FIG_56

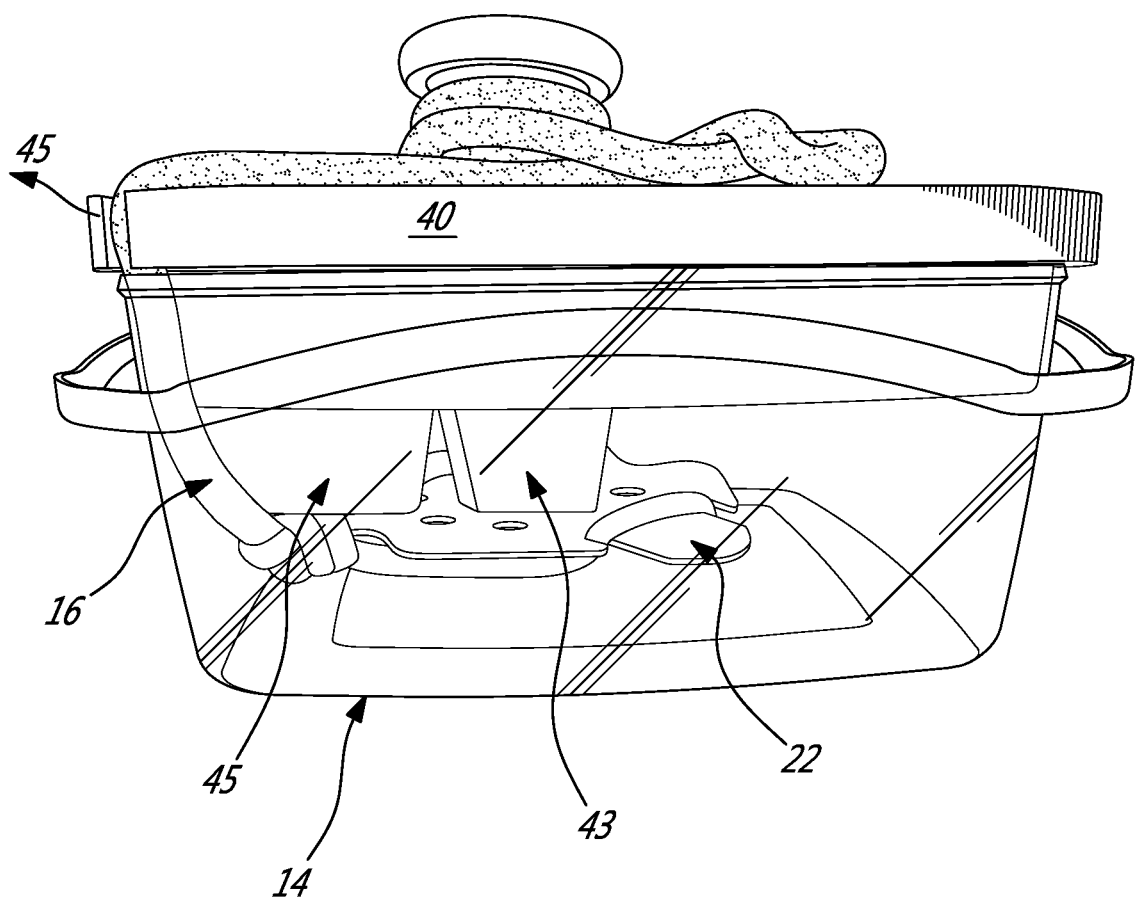
FIG_5H

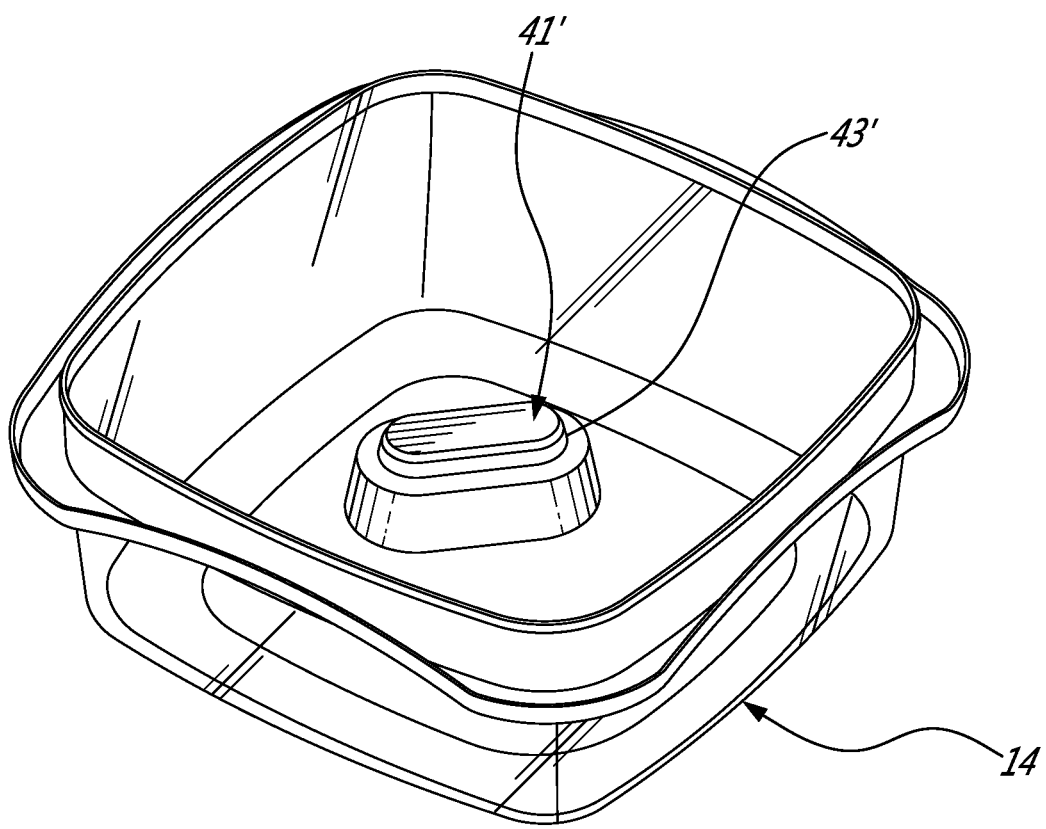
FIG_6

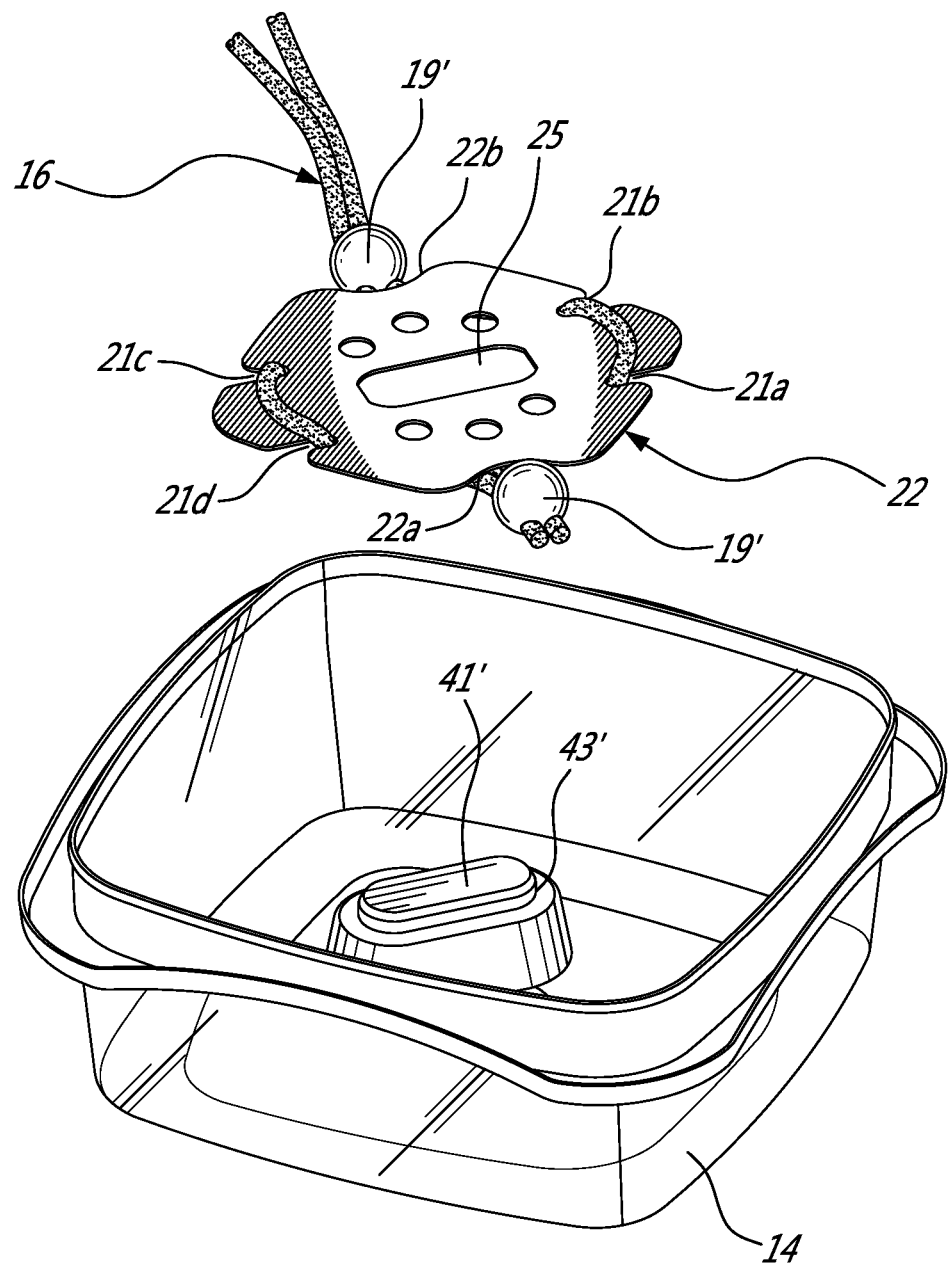
FIG_7

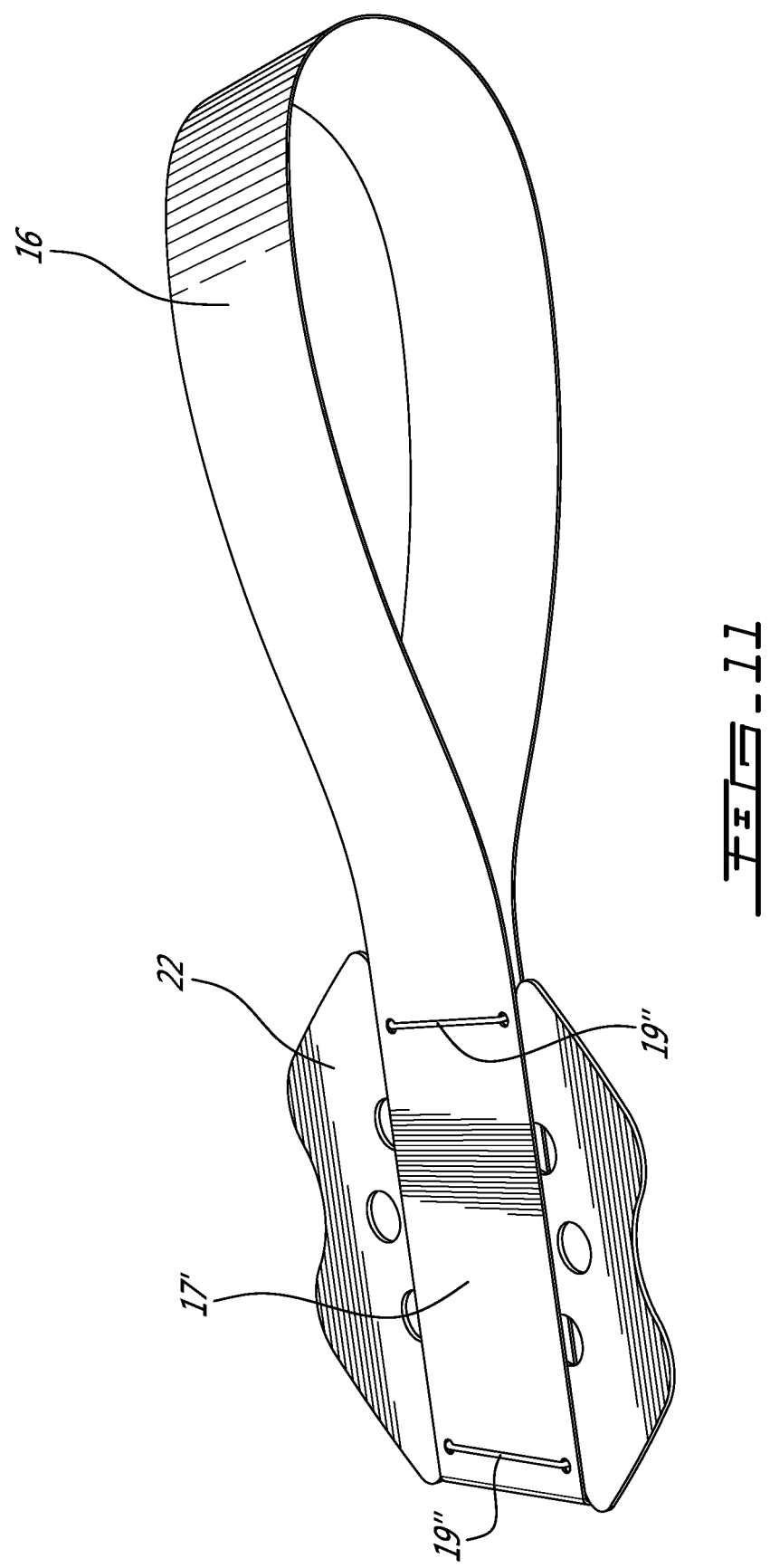

WASTE BIN ODOR CONTROL METHOD AND SYSTEM

CROSS-REFERENCE TO RELATED APPLICATIONS

This application is a National Entry Application of PCT application no PCT/CA2019/050315 filed on Mar. 14, 2019 and published in English under PCT Article 21(2), which itself claims benefit of U.S. provisional application Ser. No. 62/642,747, filed on Mar. 14, 2018. All documents above are incorporated herein in their entirety

FIELD OF THE INVENTION

The present disclosure relates to containers. More specifically, the present disclosure is concerned with an odor control method and system for containers such as waste bins.

SUMMARY OF THE INVENTION

More specifically, in accordance with the present invention, there is provided a method for making a waste bin odor-controlling pad configured to be hung within the waste bin by a connector, comprising a) providing a mold; b) providing a connector; c) positioning a first length of the connector within a mold at a predetermined position within the mold, while keeping a second length of the connector outside the mold; and d) pouring an active material within the mold; the step d) being performed before or after the step c); and the predetermined position within the mold being selected based on at least one of: i) a thickness and ii) a surface area of the pad.

There is further provided a method for making a waste bin odor-controlling pad configured to be hung within the waste bin by a connector, comprising solidifying a liquid odor-controlling material with a first length of connector embedded therein and a second length of connector extending from an outer position of the pad for hanging of the pad to a bin, in a mold, wherein the first length of connector is spread by and secured within the liquid odor-controlling material at a predetermined position within the liquid odor-controlling material during pouring and solidification of the liquid odor-controlling material by at least one of: i) a jig; ii) a wall of the mold, and iii) a cover of the mold.

There is further provided a method for controlling odor within a waste bin, comprising solidifying a liquid odor-controlling material with an first length of connector embedded therein and a second length of connector extending out of the liquid odor-controlling material, wherein the first length of connector is spread by and secured within the liquid odor-controlling material at a predetermined position within the liquid odor-controlling material during pouring and solidification of the liquid odor-controlling material into a pad, and hanging the pad within the waste bin by the second length of connector, while the first length of connector embedded within the bulk of the pad is locked within the bulk of the pad, thereby preventing tearing off therefrom under the weight of the pad and/or of items hitting the pad on their way in and out of the waste bin.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1 shows parts of a system according to an embodiment of an aspect of the present disclosure;

FIG. 2 shows a system according to an embodiment of an aspect of the present disclosure;

FIG. 3 shows a pad according to an embodiment of an aspect of the present disclosure;

FIG. 5B shows components of a system according to an embodiment of an aspect of the present disclosure;

FIG. 5D shows a jig supporting an anchor and a connector on a top side thereof according to an embodiment of an aspect of the present disclosure;

FIG. 5E shows a jig according to an embodiment of an aspect of the present disclosure;

FIG. 5F shows positioning of the connector of a pad according to an embodiment of an aspect of the present disclosure;

FIG. 5G shows positioning of the connector of a pad according to an embodiment of an aspect of the present disclosure;

FIG. 5H shows positioning of the connector of a pad according to an embodiment of an aspect of the present disclosure;

FIG. 5I shows positioning of the connector of a pad according to an embodiment of an aspect of the present disclosure;

FIG. 6 shows a container according to an embodiment of an aspect of the present disclosure;

FIG. 7 shows a step of a method according to an embodiment of an aspect of the present disclosure;

FIG. 11 shows an anchored length of connector according to an embodiment of an aspect of the present disclosure.

DESCRIPTION OF EMBODIMENTS OF THE INVENTION

Figure 4D:
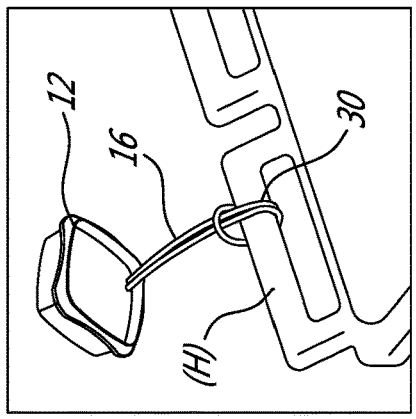
FIGS. 4A-4H illustrate steps of a method of use of a pad according to an embodiment of an aspect of the present disclosure.

FIGS. 1 to 3 shows parts of a system according to an embodiment of an aspect of the present disclosure, including a container 14, a pad 12 and a connector 16. The pad 12 is shown contained within the container 14, and a film 20 may be positioned on top of the pad in the container 14, and the container 14 closed by a cover 18.

As best seen in FIGS. 2 and 3, the connector 16 has a first end 30 embedded within the bulk of the pad 12, and a second end 32 extending out of the bulk of the pad 12 for attachment to a waste bin for example, as described hereinbelow.

Figure 4H:
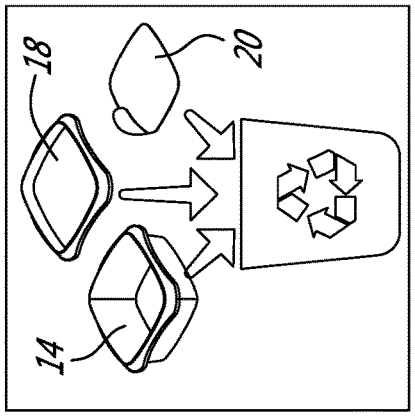
Figure 4C:
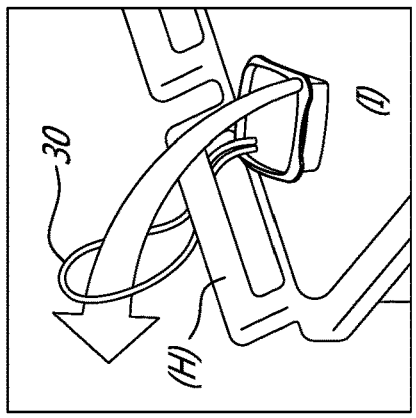
Figure 4G:
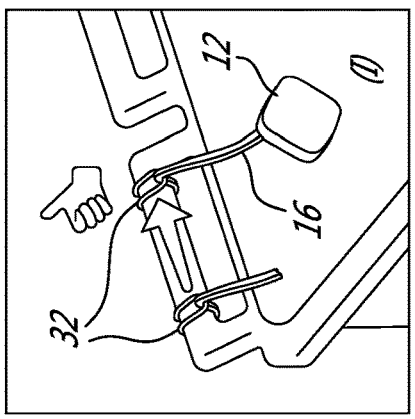
Figure 4B:
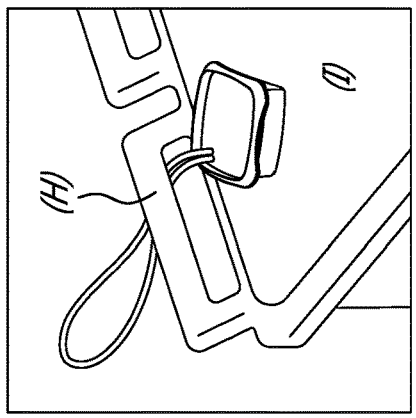
Figure 4F:
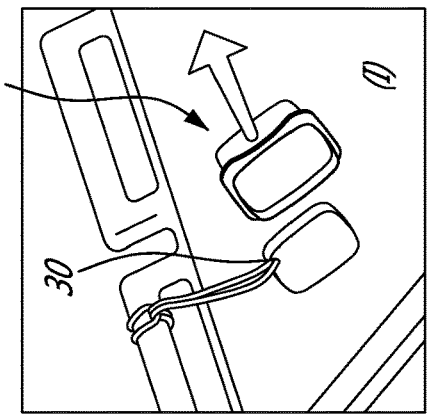
Figure 4A:
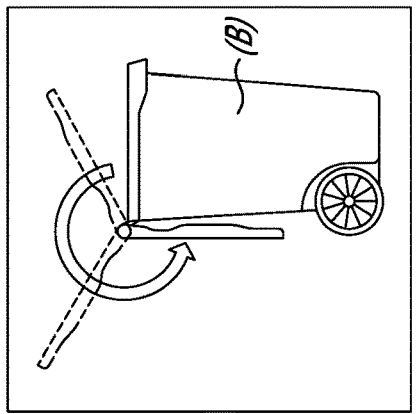
Figure 4E:
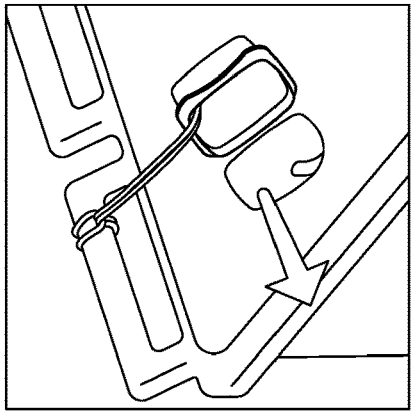

When in use as described hereinbelow, for example when the pad 12 is hung in a trash bin by the connector 16 (see for example FIG. 4G), the first end 30 of the connector 16 embedded within the bulk of the pad 12 securely locked into place within the bulk of the pad 12, thereby preventing tearing off therefrom under the weight of the pad 12 for instance or when contacted by items hitting the pad on their way in and out of the trash bin for example while the pad 12 is hung in the trash bin by the connector 16 as shown in FIG. 4G for instance.

As depicted for example in FIG. 4 in relation to a waste bin, the second end 32 of the connector 16 may be secured to a rear handle (H) of the waste bin (B) (FIGS. 4B-D), so that the pad 12 is hung in the inside (I) of the waste bin (B) (see FIG. 4G).

The material of the pad 12 is selected so as to release a fragrance and/or an odor neutralizer. The material of the pad 12 contains chemical and/or biological agents that react with odors, by reacting with pungent smelling gases for example, and/or odor sources such as bacteria, fungi, etc that may occur within a trash bin bin for example.

The nature and/or the shape and/or the geometrical characteristics including surface area for example, of the pad 12 are selected according to a target fragrance and/or neutralizer effect intensity and/or duration, according to the application, i.e. type of bin, and environment conditions, such as temperatures and humidity conditions therein for instance.

The material of the pad 12 may be selected so as to selectively react to environmental conditions, such as temperature and humidity variations; for example, the target fragrance and/or neutralizer effect may be such that it intensifies when the temperature rises for instance.

The pad 12, the connector 16 and the anchor 22 may be made in materials selected to be biodegradable and/or compostable and designed to be disposed of during collection of organic wastes in case the waste bin is an organic waste bin for example, and/or not to contaminate the content of the bin in case they fall within the bin. The connector 16 may be a length of yarn for instance; the anchor 22 may be a cardboard sheet for instance. In an embodiment illustrated in FIG. 11, the anchor 22 supports a folded length 17' of ribbon connector 16, with clips 19" as stoppers for instance.

The cover 18, the container 14 and the film 20 may be made in materials selected to be recycled, such as polypropylene or HDPE for instance (see FIG. 4H). They may be selected to be biodegradable and/or compostable, such as polylactide polymer (PLA) for example.

FIG. 5 show steps of a method according to an embodiment of an aspect of the present disclosure.

Figure 5A:
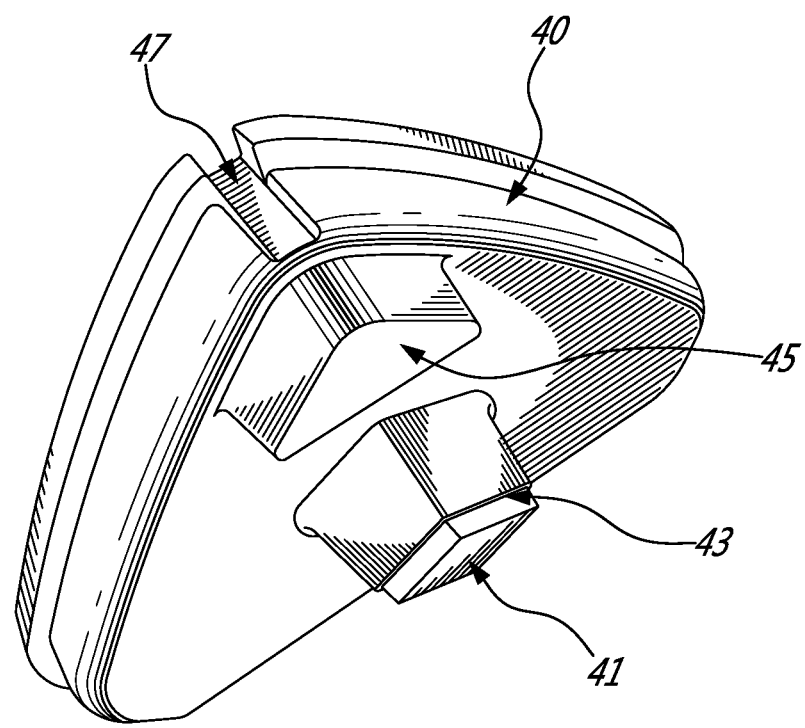
FIG. 5A shows a jig according to an embodiment of an aspect of the present disclosure.
Figure 5C:
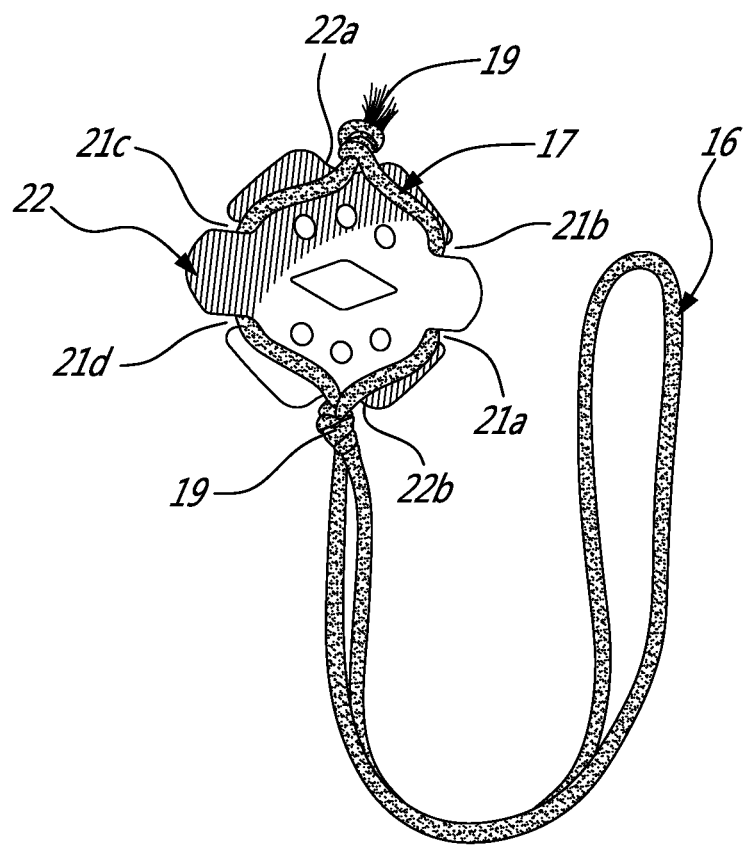
FIG. 5C shows an anchor according to an embodiment of an aspect of the present disclosure.
Figure 50:
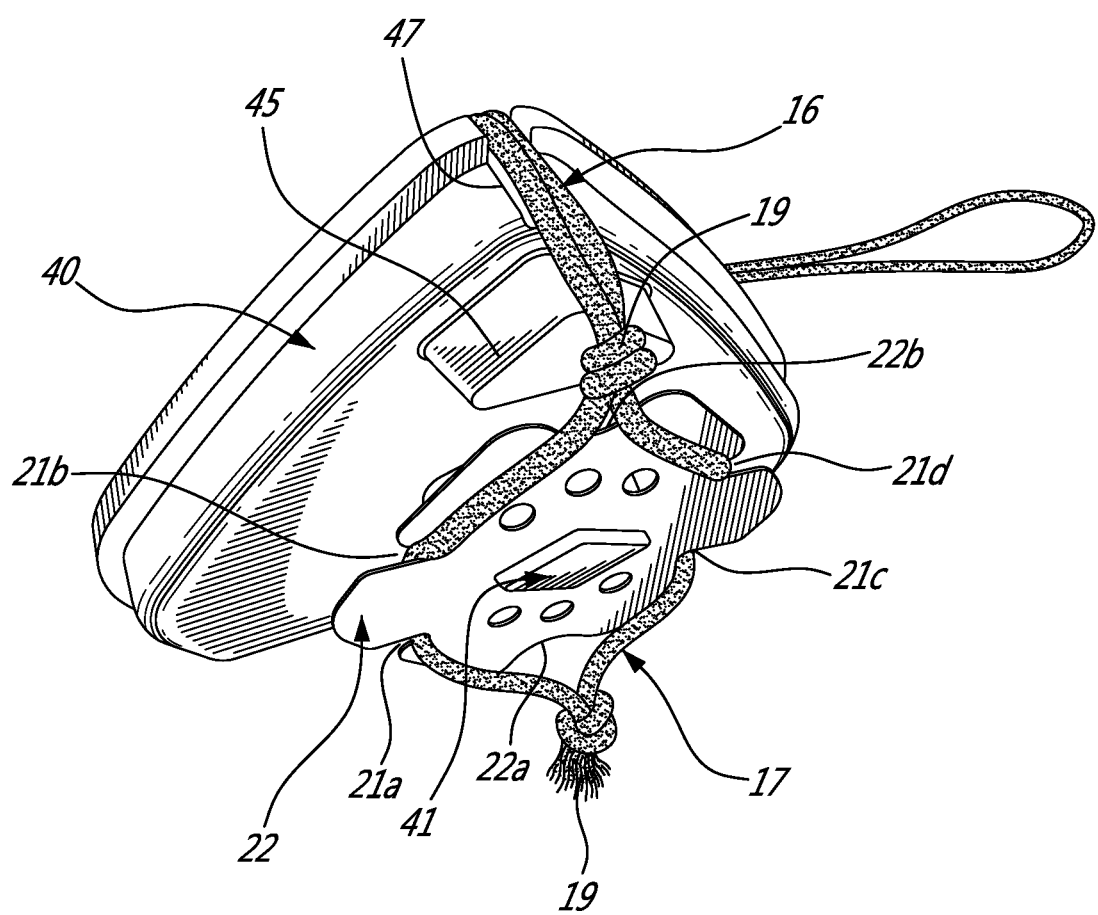
Figure 51:
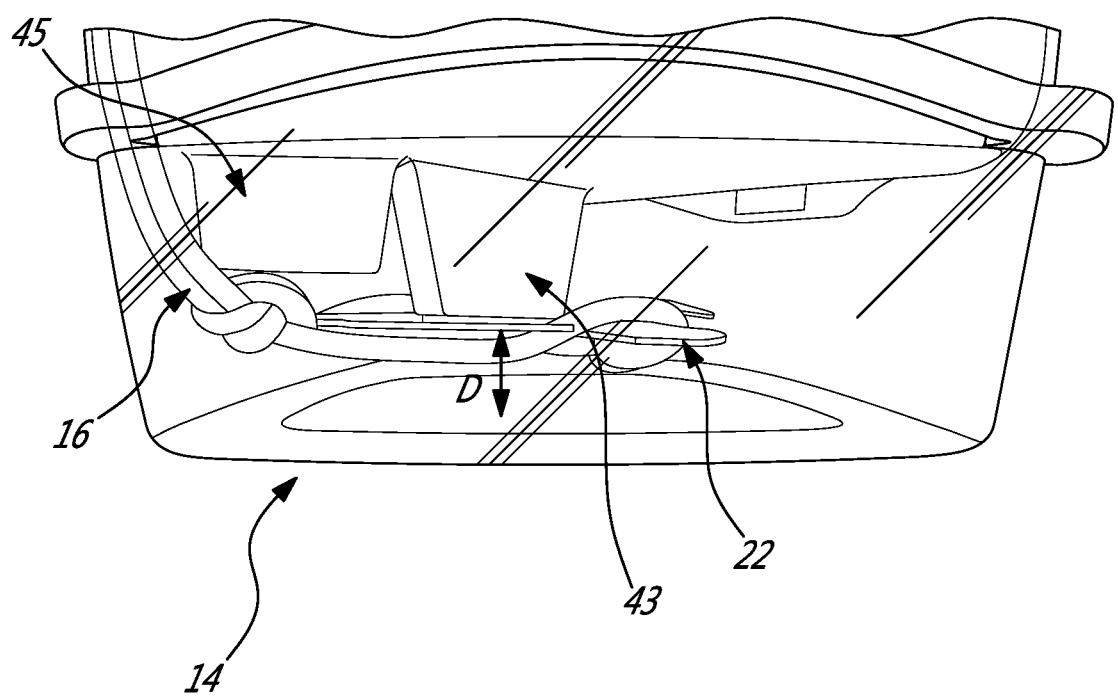

In an example illustrated in FIG. 5C, a loop 17 is formed at the first end 30 of the connector 16, by stoppers shown as two knots 19 for example, and threaded about the perimeter of the anchor 22 comprising a series of slots 21a-21d for example, so that the loop 17 is maintained opened, as shown in FIGS. 5C and 5D for example. As best seen in FIGS. 5D and 5I, the loop 17 is opened by weaving the connector 16 alternatively above and below the anchor 22 though the slots 21a-21d, so that the knots 19 are positioned below the anchor 22, i. e, in a position facing the inside of the container 14 in FIG. 5H for example. Other stoppers 19' than knots 19 may be contemplated to define the loop, or part of a loop, in an embodiment shown in FIG. 7. The loop illustrated herein is a closed loop; however, it may be open, and or a part loop. The length of loop may be thus secured to the anchor using glue or snaps or tabs or by sewing for example.

The anchor 22 with the loop 17 of the connector 16 thus secured thereto is then secured to a jig 40 (FIGS. 5A, 5D-F).

As shown in FIGS. 5A and 5D for example, the anchor 22 comprises a female connecting element such as an opening 25 and the jig 40 comprises a male element 41 that engages the aperture 25 of the anchor 22 for assembly of the anchor 22 on the jig 40.

Figure 8:
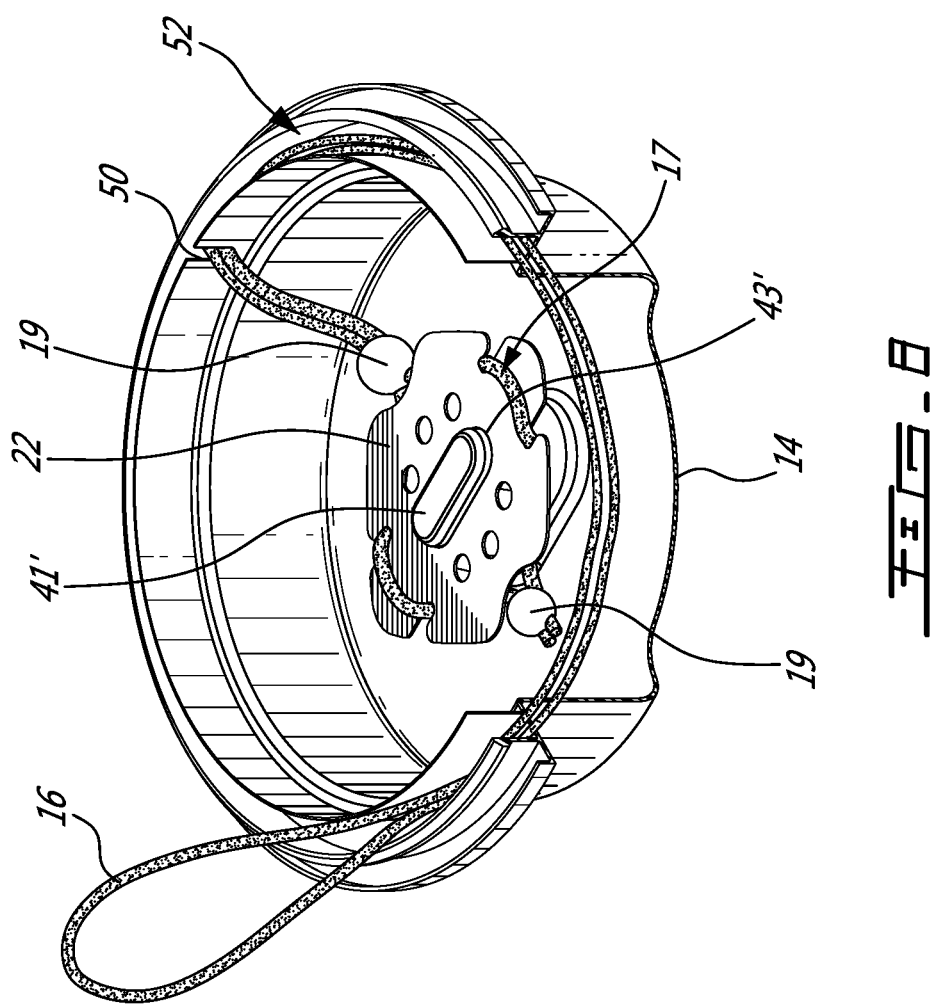
FIG. 8 shows a step of a method according to an embodiment of an aspect of the present disclosure.

The anchor 22 and the jig are removably connected together to ensure a fitted grip therebetween. FIGS. 5A-5D shows a diamond-shaped opening 25 and fitting diamond shaped male element 14, preventing relative rotation between the anchor 22 and the jig 40 (see FIG. 5D), while FIGS. 6-8 show an oblong opening 25 and fitting male element 41', preventing relative rotation between the anchor 22 and the container 14.

The jig or container may alternatively comprise a female element and the anchor a corresponding male element, or any combination thereof.

The jig 40 thus holding the loop 17 of the connector 16 on a first side thereof, is positioned relative to the container 14, the anchored loop 17 facing towards the inside of the container 14. As the material of the pad 12 is poured within the container 14 in a liquid form, the anchored loop 17 is thus immersed within the material of the pad 12, the top side of the jig 40 remaining out of the liquid (FIGS. 5G-5H).

The anchored loop 17 is maintained opened and spread generally horizontally within the depth the liquid active material of the pad 12 as it solidifies within the container (FIGS. 5G-1), whereas the remaining length of the connector 16 is kept out of the way by the jig 40 (FIG. 5G). Then the connector 16 is untied from the top side of the jig 40 and the jig 40 is retrieved by pulling it from the molding container to unlock it and disengage it from the anchor, which remains embedded within the pad, leaving the loop 17 embedded within the pad 12 as shown in FIG. 2 for example.

In FIG. 5A, the male element 41 is provided with a shoulder 43 defining the height at which the anchor 22 is held by the jig 40 from the free tip of the male element 41 of the jig 40, thereby allowing controlling the depth D of the loop 17 within the active material, and hence the depth of the loop 17 of the connector 16 within the bulk of the pad 12 (See FIG. 5I).

Besides a corrugated perimeter, illustrated with circumferential slots or recesses herein for example, allowing opening of the loop of the connector, the anchor 22 is provided with vents 23 (see FIG. 5B) allowing air bubbles to escape from underneath the anchor 22 up to the surface of the active material during solidification of the active material so as to provide a resulting solidified active material pad essentially free of voids. Moreover, they allow formation of mechanical bridges between the parts of the pad 12 on each side of the anchor 22.

Alternatively, the pad 12 may be poured within the container 14, and the anchor 22 with the loop 17 secured thereto dipped therein using the jig 40 before solidification of the pad 12.

At least one protrusion 45 may be provided on the bottom side of the jig 40 as shown in FIG. 5A, which supports a length of the connector 16 starting from the end of the loop 17 secured by the anchor 22 and guides it to a slot 47 on an edge or a side of the jig 40 connecting the bottom side of the jig to the upper side of the jig (see FIGS. 5E, 5D). Thus, the loop 17 remains open and spread within the material of the pad 12 while the free length of connector 16 is neatly kept out thereof, during pouring of the liquid and/or solidification of the active material and before the active material is solid and after the pad is formed (see FIGS. 5F-5H).

In an example illustrated in FIG. 5G, a knob 47 on the upper side of the jig 40 allowing handling the jig 40 is also used for storing the length of connector 16 emerging from underneath the jig 40 during pouring of the liquid and/or solidification of the active material. Alternatively, cable clips for example may be used to secure the extra length of connector 16.

The jig 40 is found to allow a precise positioning of the loop 17 of connector well open and spread by the anchor 22, spatially within the bulk of pad 12, i.e. according to all x, y and z axis, generally centered within the bulk of the pad, i.e. relative to the thickness and the surface area of the pad, thereby ensuring a strong anchorage of the connector within the pad 12, so that hen in use as illustrated for example in FIG. 4G, the pad 12 hangs generally flat against an inside wall of a trash bin, unobtrusively, securely held by the connector 16 even when hit by an object thrown within the bin and/or ejected therefrom during waste collection for instance.

In the embodiment described hereinabove, the pad is molded directly within the container that is used for packaging and storing the pad before use for example. Alternatively, the pad may be molded in a container dedicated for molding only.

The anchor was described with one female opening 25 and the jig 40 with a corresponding male element 41, although the anchor may comprise a plurality of female openings and the jig a matching plurality of male elements. Still alternatively, the anchor may be provided with at least one male and/or female element and the jig with at least one corresponding female and/or male element. Also, the respective corresponding connecting elements between the anchor and the jig/the base of the molding container are shown generally centered on the surface of the anchor; alternatively, they may be provided on the circumference of the anchor for a connection to the jig/a wall of the molding container, by the perimeter of the anchor for example.

Alternatively, instead of a jig, the container 14 and/or the cover 18 may be provided with a connecting element such as a male element 41' with a shoulder 43' supporting the anchor 22; as illustrated FIGS. 6 to 9 for example.

Figure 9:
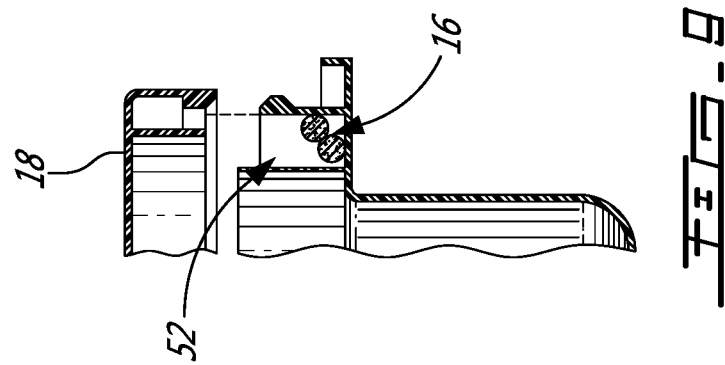
FIG. 9 shows a detail of FIG. 8.

In an embodiment illustrated in FIGS. 8 and 9 for example, the anchor 22 is thus positioned and maintained in position at a target position within a molding container, such as the container 14 for instance, by the male element 41' standing from the inner surface of the bottom wall of the molding container. The thus anchored loop 17 is maintained opened and spread generally horizontally within the depth of the liquid active material of the pad as it solidifies within the molding container. The remaining length of the connector 16 may be kept out of the way, for example by storage within a housing 52 of the molding container outside the molding container inner volume and accessible from the inner volume by a guiding slot 50 as exemplified in FIGS. 8 and 9. When the pad is demolded and the length of connector 16 is freed from the container, the loop 17 remains embedded within the pad, yielding a pad usable in a bin as shown in FIG. 4G for instance.

The shoulder 43' defines the height at which the anchor 22 is held above the base of the bottom wall of the molding container, and hence the depth of the loop of connector within the bulk of the pad 12.

Figure 10:
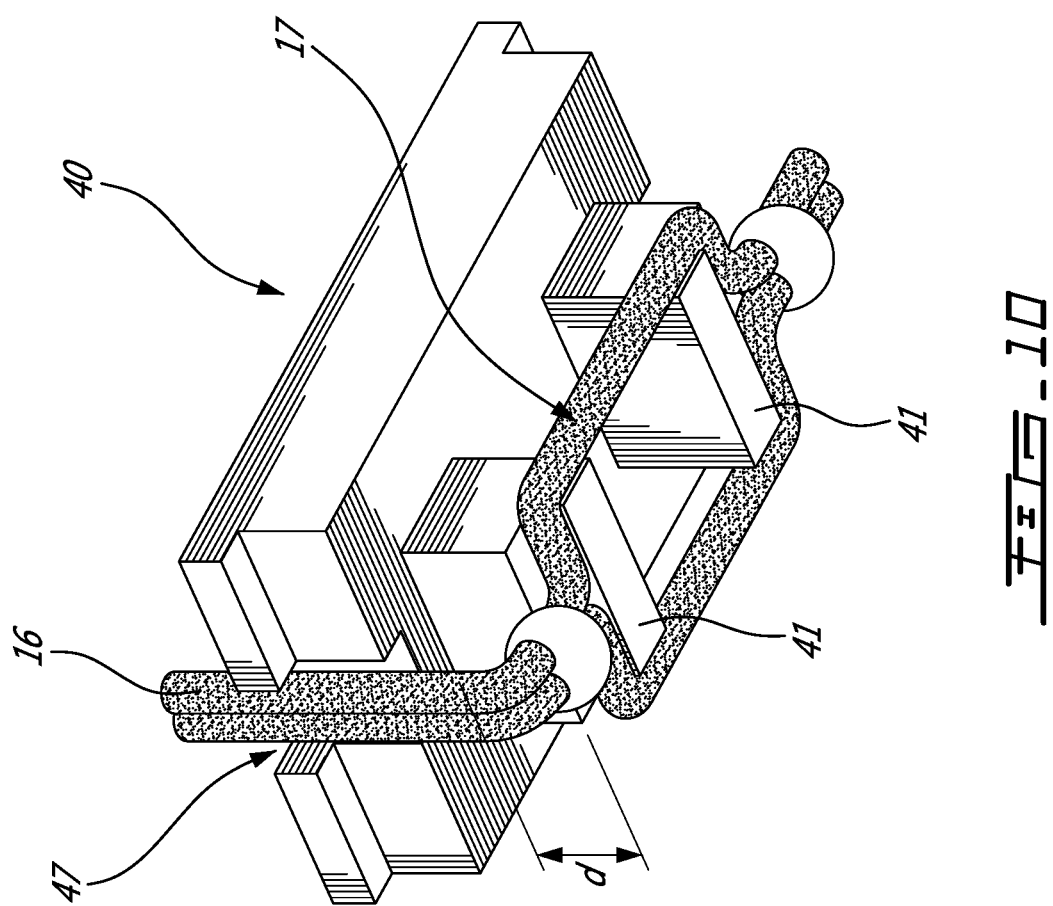
FIG. 10 shows a jig according to an embodiment of an aspect of the present disclosure.

In an embodiment illustrated in FIG. 10, the jig 40 comprises two male elements 41 on the bottom side thereof, and the loop 17 of connector 16 is formed around these male elements 41, and secured at a distance (d) from the bottom side of the jig 40 by male elements 41. In this example, an anchor as described hereinabove is not required. As mentioned hereinabove. Instead of a jig, the container 14 and/or the cover 18 may be provided with corresponding elements that secure a length of connector deployed within the liquid during pouring of the liquid and/or solidification of the active material.

The scope of the claims should not be limited by the embodiments set forth in the examples, but should be given the broadest interpretation consistent with the description as a whole.

What is claimed is:

1. A method for making a waste bin odor-controlling pad configured to be hung within the waste bin by a connector, comprising:
    a) providing a mold;
    b) providing a connector;
    c) positioning a first length of the connector within the mold at a predetermined position within the mold, while keeping a second length of the connector outside the mold; and
    d) pouring an active material within the mold;
        said step d) being performed before or after said step c);
        the predetermined position within the mold being selected based on at least one of: i) a thickness and ii) a surface area of the pad,
        wherein said step c) comprises forming at least one part of a loop of the connector; and positioning the at least one part of the loop within the mold at the predetermined position within the mold, while keeping the second length of the connector outside the mold, securing the at least one part of the loop to an anchor and positioning the anchor at the predetermined position within the mold, said securing the at least one part of the loop to the anchor comprising one of: i) gluing, ii) sewing and iii) clipping the at least one part of the loop to the anchor.

2. The method of claim 1, wherein said securing the at least one part of the loop to the anchor comprising defining the at least one part of the loop by stoppers, said step d) of positioning the at least one part of the loop within the mold comprising positioning the anchor at the predetermined position within the mold with the stoppers positioned in a position below the anchor.

3. The method of claim 1, wherein, said positioning the anchor at the predetermined position within the mold comprising removably fitting the anchor to a jig, and positioning the jig thus supporting the anchor supporting the at least one part of the loop on a first side thereof relative to the mold in such a way that the anchored at least one part of the loop is positioned at the predetermined position within the mold.

4. The method of claim 1, wherein, said positioning the anchor at the predetermined position within the mold comprising removably fitting the anchor to a jig, and positioning the jig thus supporting the anchor supporting the at least one part of the loop on a first side thereof relative to the mold in such a way that the anchored at least one part of the loop is positioned at the predetermined position within the mold, and wherein the anchor is removably fitted to the jig by at least one of male/female elements.

5. The method of claim 1, wherein, said positioning the anchor at the predetermined position within the mold comprising removably fitting the anchor to a jig, and positioning the jig thus supporting the anchor supporting the at least one part of the loop on a first side thereof relative to the mold in such a way that the anchored at least one part of the loop is positioned at the predetermined position within the mold, and wherein the anchor comprises an opening and the jig comprises a fitting male element.

6. The method of claim 1, wherein, said positioning the anchor at the predetermined position within the mold comprising removably fitting the anchor to a jig, and positioning the jig thus supporting the anchor supporting the at least one part of the loop on a first side thereof relative to the mold in such a way that the anchored at least one part of the loop is positioned at the predetermined position within the mold, and wherein the jig supports the anchor supporting the at least one part of the loop within the active material and guiding the remaining length of connector out of the mold during solidification of the active material.

7. The method of claim 1, wherein, said positioning the anchor at the predetermined position within the mold comprising removably fitting the anchor to a jig, and positioning the jig thus supporting the anchor supporting the at least one part of the loop on a first side thereof relative to the mold in such a way that the anchored at least one part of the loop is positioned at the predetermined position within the mold, the method further comprising pouring the active material within the mold, and retrieving the jig from the mold after solidification of the active material about the anchor supporting the at least one part of a loop.

8. The method of claim 1, wherein the anchor is removably fitted to a base wall of the mold by at least one of male/female elements.

9. The method of claim 1, wherein the anchor is removably fitted to a base wall of the mold by at least one of male/female elements, and wherein the wall of the mold supports the anchor supporting the at least one part of the loop within the active material and guiding the remaining length of connector out of the mold during solidification of the active material.

10. The method of claim 1, wherein said positioning the anchor at the predetermined position within the mold comprises fitting the anchor to a cover.

11. The method of claim 1, wherein said positioning the anchor at the predetermined position within the mold comprises fitting the anchor to a cover and wherein the cover supports the anchor supporting the at least one part of the loop within the active material during solidification of the active material.

\* \* \* \* \*